(12) United States Patent
Bergner et al.

(10) Patent No.: US 7,284,858 B2
(45) Date of Patent: Oct. 23, 2007

(54) METHOD FOR DETERMINING DISTANCES IN THE ANTERIOR OCULAR SEGMENT

(75) Inventors: Roland Bergner, Jena (DE); Roland Barth, Jena (DE); Axel Doering, Jena (DE); Frank Behrend, Jena (DE); Klaus-Ditmar Voigt, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 630 days.

(21) Appl. No.: 10/468,241

(22) PCT Filed: Feb. 16, 2002

(86) PCT No.: PCT/EP02/01675

§ 371 (c)(1),
(2), (4) Date: Aug. 18, 2003

(87) PCT Pub. No.: WO02/065899

PCT Pub. Date: Aug. 29, 2002

(65) Prior Publication Data

US 2004/0070728 A1 Apr. 15, 2004

(30) Foreign Application Priority Data

Feb. 21, 2001 (DE) ............................ 101 08 797

(51) Int. Cl.
*A61B 3/10* (2006.01)
(52) U.S. Cl. .................. 351/205; 351/206; 351/208
(58) Field of Classification Search ............ 351/205, 351/206, 208–212, 221, 246; 396/51; 382/103, 382/117, 128, 276
See application file for complete search history.

(56) References Cited

U.S. PATENT DOCUMENTS 4,319,564 A 3/1982 Karickhoff (Continued)

FOREIGN PATENT DOCUMENTS

DE 196 41 632 A1 5/1997

(Continued)

OTHER PUBLICATIONS

International Search Report.

*Primary Examiner*—Huy Mai
(74) *Attorney, Agent, or Firm*—Patterson, Thuente, Skaar & Christensen, P.A.

(57) ABSTRACT

The invention relates to a method for determining distances in the anterior ocular segment, preferably of the pupils and/or the diameter of the iris, wherein the image of at least part of the eye is recorded and digitized using an imaging device and an array for illuminating the eye. On the basis of said digital image, a center of gravity analysis and the determination of the central point are carried out, especially for the position of the pupils, by conducting an intensity and threshold analysis as rough determination. Based on said rough determination, a fine detection of the position of the edges of the pupil and/or the edges of the iris is carried out. Additionally, the angle between the visual axis and the optical axis of the eye can be determined from the position of a fixed reflection to the center of the pupil and/or the center of the iris.

18 Claims, 9 Drawing Sheets

U.S. PATENT DOCUMENTS

| | | | |
|---|---|---|---|
| 4,398,812 A | 8/1983 | Kelman | |
| 4,812,033 A * | 3/1989 | Ishikawa | 351/208 |
| 5,036,347 A | 7/1991 | Tsunekawa et al. | |
| 5,071,245 A | 12/1991 | Fukuma et al. | |
| 5,231,674 A | 7/1993 | Cleveland et al. | |
| 5,327,191 A | 7/1994 | Shindo et al. | |
| 5,428,413 A * | 6/1995 | Shindo | 351/210 |
| 5,474,548 A | 12/1995 | Knopp et al. | |
| 5,491,757 A * | 2/1996 | Lehmer et al. | 382/128 |
| 5,671,447 A * | 9/1997 | Tokunaga | 396/51 |
| 5,790,235 A | 8/1998 | Kirschbaum | |
| 5,797,046 A * | 8/1998 | Nagano et al. | 396/51 |
| 5,822,033 A | 10/1998 | Ishikawa et al. | |
| 5,835,797 A * | 11/1998 | Odaka | 396/51 |
| 5,887,200 A * | 3/1999 | Aoyama | 396/50 |
| 5,889,577 A * | 3/1999 | Kohayakawa | 351/211 |
| 5,913,079 A * | 6/1999 | Aoyama et al. | 396/51 |
| 6,035,054 A * | 3/2000 | Odaka et al. | 382/117 |
| 6,081,607 A | 6/2000 | Mori et al. | |
| 6,322,216 B1 * | 11/2001 | Yee et al. | 351/210 |
| 6,419,638 B1 * | 7/2002 | Hay et al. | 600/558 |
| 6,611,283 B1 * | 8/2003 | Isonuma | 348/51 |
| 6,779,891 B1 * | 8/2004 | Barth et al. | 351/212 |
| 2002/0049431 A1 * | 4/2002 | Smith et al. | 606/5 |
| 2004/0070728 A1 * | 4/2004 | Bergner et al. | 351/206 |

FOREIGN PATENT DOCUMENTS

| | | |
|---|---|---|
| DE | 196 18 883 A1 | 11/1997 |
| DE | 196 49 542 C2 | 4/1998 |
| EP | 0 821 912 A2 | 2/1998 |
| JP | 02000004 A | 1/1990 |
| JP | 05-168597 | 7/1993 |
| JP | 05285113 A | 11/1993 |
| JP | 06-277182 | 10/1994 |
| JP | 07-136115 | 5/1995 |
| JP | 07174541 A | 7/1995 |
| JP | 07-249197 | 9/1995 |
| JP | 08-238222 | 9/1996 |
| JP | 09-192101 | 7/1997 |
| JP | 10040375 A | 2/1998 |
| JP | 10057319 A | 3/1998 |
| WO | WO92/05736 | 4/1992 |
| WO | WO97/42920 | 11/1997 |
| WO | WO 00/33729 | 6/2000 |

* cited by examiner

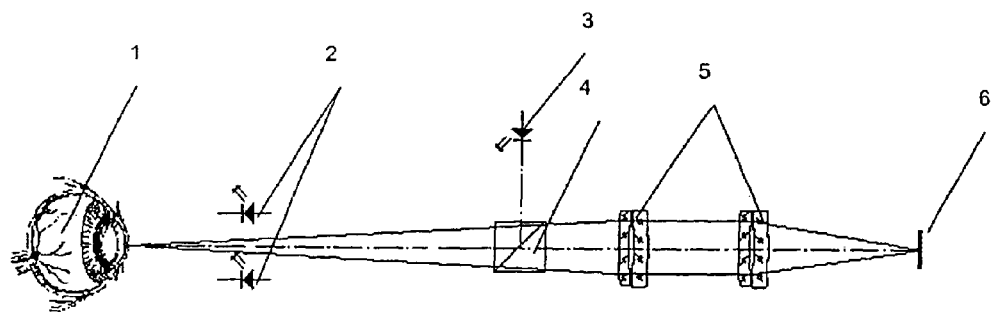
Fig. 8 schematische Darstellung der erfindungsgemäßen Anordnung
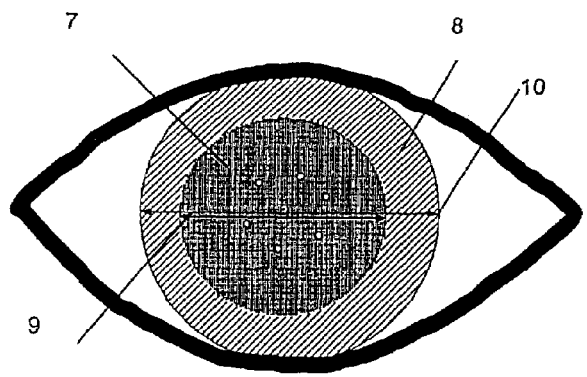
Fig. 9 gegrabbtes Bild eines zu vermessenden Auges
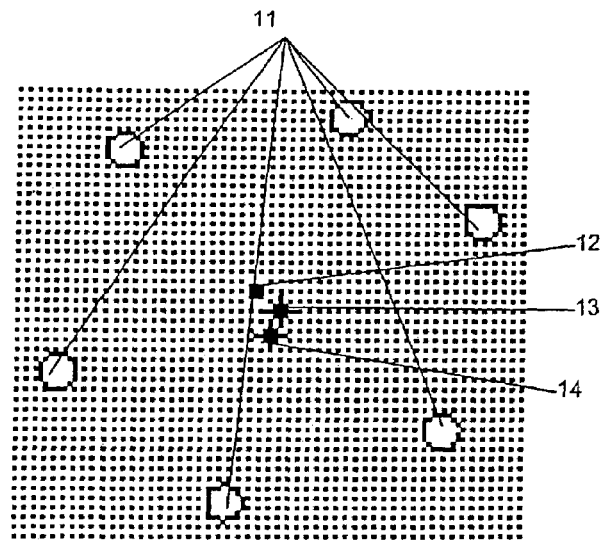
Fig. 10 Vergrößerung des zentralen Teiles von Fig. 9

Fig.11 Weiß-zu-Weiß-Schablone nach Holladay-Godwin:
AE-1576 Holladay-Godwin
Cornea Guage
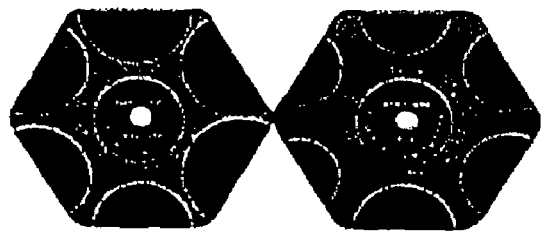

METHOD FOR DETERMINING DISTANCES IN THE ANTERIOR OCULAR SEGMENT

The IOL (intraocular lens) calculation formula "Holladay 2" ("Intraocular Lens Power Calculations for the Refractive Surgeon", Jack T. Holladay, in: Operative Techniques in Cataract and Refractive Surgery, Vol. 1, No. 3 (September), 1998: pp 105-117), by which the power of an intraocular lens (IOL) for implantation into the human eye can be calculated, as well as the selection of special types of IOL (ICL etc.), require the so-called "horizontal white-to-white distance" (hor-w-t-w), which is the horizontal diameter of the iris, as an input value.

In corneal surgery for the removal of visual deficiciencies in the human eye (PRK, LASIK), it is also interesting for the surgeon to know at which point the patient's visual axis passes through the cornea. Thereafter, laser ablation can be effected more precisely at this point than according to the previous assumption based on the geometric center of the cornea.

The interferometric length measurement of the thickness of the cornea, of the anterior chamber depth and of the lens thickness in the human eye using PCI requires preadjustment of the eye along its theoretical optical axis in front of the measurement instrument, as opposed to the axial length measurement which requires positioning of the eye along the actual visual axis.

In order to determine the "hor-w-t-w", use was previously made of rulers and templates (FIG. 11, which are held in front of the patient's eye and from which the diameter of the iris is thus read by taking a fix. This method is susceptible to interference by parallax during observation, and the templates previously used have a 0.5 mm grading, allowing only limited precision. Another known solution are measuring eyepieces employed as fittings on slit lamp devices (Instruction Manual for slit-lamp 30 SL/M, publication no.: G 30-114-d (MAX1/79) Carl Zeiss D-7082 Oberkochen, page 38). Although such eyepieces prevent parallax errors, the diameter value has to be read from a scale.

Further, invasive measurement means are known in the form of mechanical slide gauges which are inserted into the anterior chamber through an incision in the sclera (e.g. U.S. Pat. No. 4,319,564).

Further, gonioscopes, as they are called, are known which are placed on the eye, project scales onto the iris and allow the iris diameter to be read through magnifying glasses (e.g. U.S. Pat. No. 4,398,812).

Devices which measure the diameter of the pupil are referred to as pupillometers (e.g. EP 0,550,673). However, they do not measure the diameter of the iris.

No devices are known for determining the point where the visual axis passes through the cornea. The camera industry merely uses methods which detect the direction in which a human eye is looking; the output signals of such arrangements serve, for example, to control autofocus mechanisms in photographic cameras (e.g. U.S. Pat. No. 5,291,234), or they are used in so-called eye trackers. Said devices monitor eye movements or viewing movements.

Also, no devices are known for preadjustment of the eye along the optical axis; by focusing the eye differently or by scanning the measuring beam, rather haphazard efforts are made to find the right positioning of the eye along the optical axis by trial.

The applicant's WO 00/33729 discloses a system and a method for determining, in a non-contacting manner, the axial length, the cornea curvature and the anterior chamber depth of the eye using one single device to calculate the optical effect of an intraocular lens. The eye is generally illuminated via visible or IR LEDs, the reflection images thereof being captured by the CCD camera and displayed. Further, a fixation light is provided for the test subject to direct the pupil of the eye in the direction of the optical axis, the reflection of the fixation light also being captured by the CCD camera.

It is an object of the invention to provide a device and a method allowing higher precision of the hor-w-t-w determination in a user-independent manner. According to the invention, this object is achieved by the features of the independent claims. Preferred further embodiments are the subject of the dependent claims.

In a surprising manner, the invention also realizes a practical possibility of describing the point of intersection of the visual axis through the cornea relative to the center of the pupil and/or the center of the iris and of enabling a more precise preadjustment of an interferometric length measurement instrument along the optical axis of the eye, based on the position of said intersection point and on the geometric center of the cornea.

The position of the visual axis was previously unknown to the user of such instrument. Therefore, the patient was requested to focus differently by suitable means (fixation light for the patient's eye within the instrument or outside the instrument). Thereupon, a measurement operation was initiated, which was only successful if the measurement was effected along the optical axis. This means that it is not clear whether or not this axis has been hit until after said measurement operation.

The fixation light is moved in increments of 1°; quite a few useless measurement operations may be required until the point is reached where said interferometric measurement is successful.

Such procedure is not acceptable in the ophthalmological routine.

Embodiment example:

The invention is described in greater detail below with reference to the schematic drawings, wherein:

FIG. 8 shows the illumination beam path/detection beam path,

FIG. 9 is an overview over the eye to be measured,

FIG. 10 is an enlarged view of the center of FIG. 9,

FIG. 11 shows a white-to-white gauge according to Holladay-Godwin.

Figure 1:
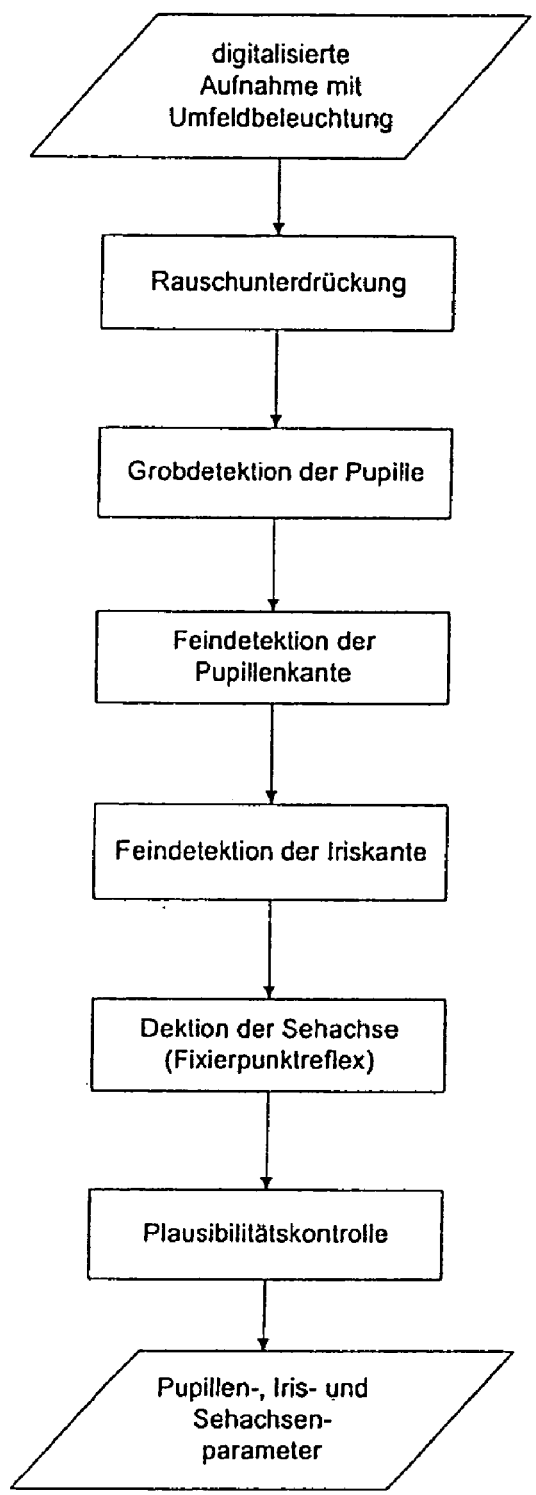
FIG. 1 is a flowchart of the method according to the invention.

According to FIG. 8, the eye 1 of the test subject is illuminated by preferably infrared-light emitting light sources 2, which are arranged in a circle around the optical axis, as in WO 00/33729 (e.g. LED). A light source 3, onto which the test subject focuses, is faded in at the observation system, coaxially to the observation beam path, by a beam splitter 4, said light source 3 emitting visible light (e.g. LED or laser diode).

The image of the eye is imaged, via a telecentric imaging system 5 onto an image sensor 6, preferably a CCD camera, which is connected to a control and evaluation unit (not shown). The video signal of the camera is displayed on a screen or LC display (not shown).

The illumination 2 allows the user, during the entire time of adjustment and of measurement of the test subject, to check whether the test subject is focusing correctly—and, consequently, whether the result of said measurement is correct. The imaging of the test subject's eye with the relevant image details is effected in a telecentric manner so as to minimize the influence of the adjustment of the test subject.

Upon correct adjustment of the patient's eye and upon initiation by the user, the BAS signal of the CCD camera is taken over into the memory of a computer via a frame grabber. FIG. 9 schematically shows such image, including pupil 7, pupil diameter 9, as well as iris 8 and iris diameter 10. FIG. 10 shows an enlarged segment of the pupil with reflection points 11 of the illumination, the image of the fixation light 12, the iris center 13 and the pupil center 14.

Using means of image processing, the distances within said image are determined, from which the following values can be calculated on the basis of the image scale of the observation optics:

the diameter and the center of the iris,
the diameter and the center of the pupil,
the x and y coordinates of the cornea image of the fixation light (1$^{st}$ Purkinje image) relative to the center of the iris, and
the x and y coordinates of the cornea image of the fixation light (1$^{st}$ Purkinje image) relative to the center of the pupil.

Since the real shapes of the iris and pupil of the human eye do not necessarily have to be circles, ellipses with their parameters of semiaxes and focal points may be determined as well, according to a further embodiment.

With a suitably selected image scale of the imaging optics 5, the measured values can be determined with a computational precision of <±0.01 mm.

The diameter of the iris yields the horizontal white-to-white distance:

white-to-white [in mm]=$\circ_{iris}$ [in pixels]/number of pixels per mm.

The x and y coordinates of the Purkinje image of the fixation light yield the point where the visual axis passes through the cornea, provided that the test subject is focusing correctly, which the user can check during measurement on the basis of the live video image on the LC display. The visual axis and optical axis may deviate from each other by up to 8°, because the fovea may be offset from 3° nasally to 8° temporally. (Simplified schematic eye according to Gullstrand in Diepes "Refraktionsbestimmung" Bode publishing company, Pfortzheim, 5$^{th}$ edition 1988).

The angle between the visual axis and the optical axis of the eye results from angular relationships, for example, on the basis of the Gullstrand eye, wherein the measured offset (distance) between the image of the fixation point and the iris center and/or the pupil center is taken into account.

Prior to the interferometric measurement of the anterior ocular media, the deviation of both visual axes from one another is determined.

The fixation point of the present measurement system is marked along the visual axis. The amount and the direction of the distance of this point to the center of the pupil (and/or the center of the iris) is determined.

Simple trigonometric formulae yield the required angle between the optical axis and the visual axis, for example, as:
α=arc tan (a/k)

α—angle between visual axis and optical axis
α—distance between fixation point and pupil center (iris center)
k—distance between nodal point (see Diepes reference) and cornea minus R/2 (approximately 3.8 mm).

According to this measured value, a preadjustment of the patient's viewing direction may advantageously be effected by providing a fixation light to the patient at the calculated angle α, thus obviating a complex search procedure.

Method for Determining the Positions of Pupil, Iris and Fixation Point

Flowchart (FIG. 1):

As input value for evaluation, a digitized gray scale image is used at an image scale allowing the entire iris to be captured with turned-on surround field illumination.

After noise reduction, the evaluation unit determines the objects: pupil, iris and fixation point image.

Advantageously, the pupil image is roughly determined at first and used for iris detection, since the contrast at the iris edge is usually weak and, moreover, the iris periphery may be covered by the eye lids at the top and bottom thereof, so that no circular, but only sector-shaped sensing is possible.

Upon successful execution, the parameters of the iris and of the pupil are returned as a circular model (radius, center) or as an elliptic model (main axes, center). The fixation point (i.e. the point where the visual axis passes through the cornea) is returned in the form of its coordinates, i.e. the coordinates are available to the calling program.

Noise Reduction

Edge detection on the basis of gray scale profiles in the original image leads to great variations in determining the edge locations, said variations resulting from noise superpositioned on the image signal. A 20×20 median filter is used for noise reduction.

Figure 2:
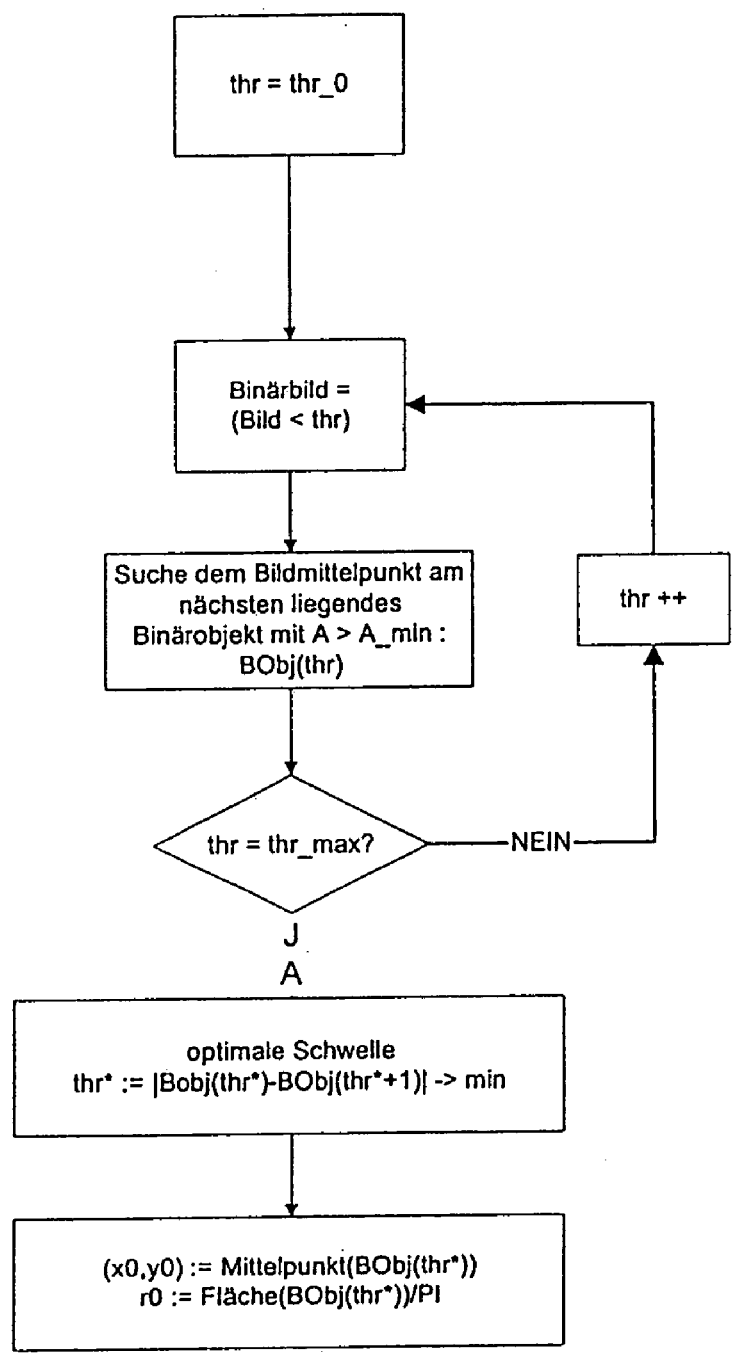
FIG. 2 shows the algorithm for rough detection of the pupil.
Figure 3:
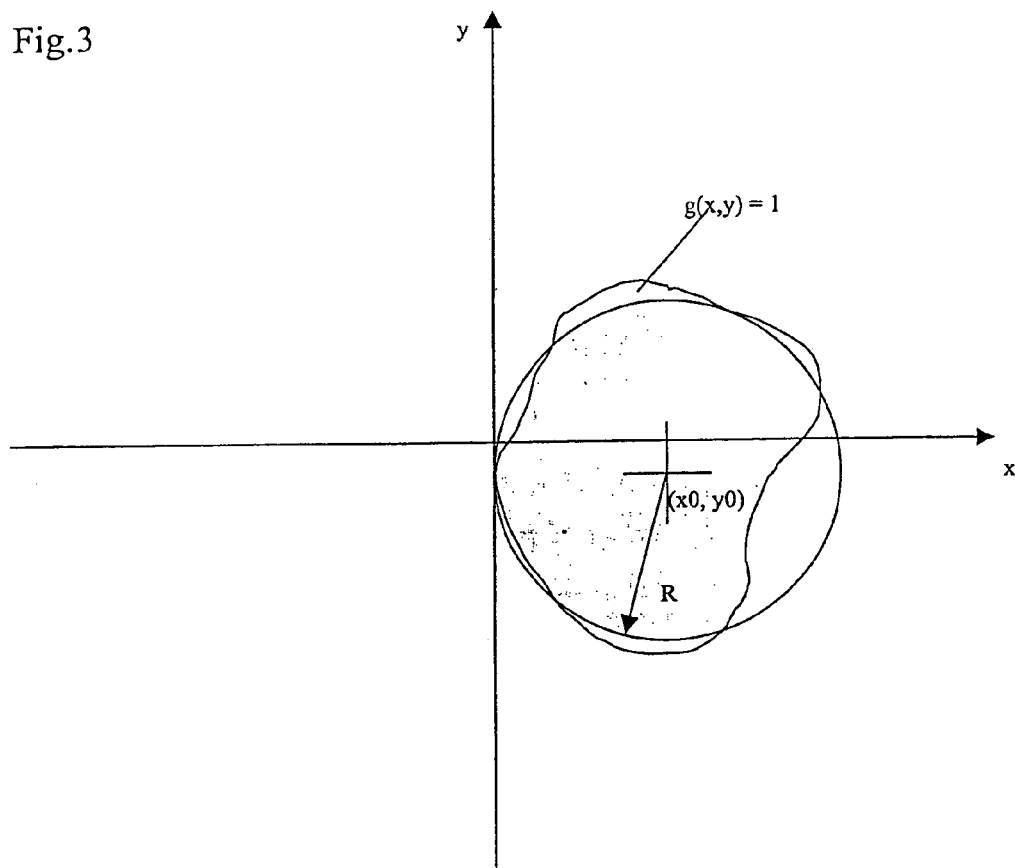
FIG. 3 represents the gray scale analysis/center determination.

Rough Detection of the Pupil—FIG. 2/FIG. 3

For rough detection of the position of the pupil, a binarization method with subsequent search for joined objects in the binary image is used.

FIG. 3 shows an uneven gray scale distribution g (x,y), sensed by the CCD camera and determined by threshold value analysis (threshold value 1), in an X/Y coordinate system. The theoretical center xo,yo of this area is determined by a centroid analysis, and a circular model/elliptical model having a radius R is determined. (This will be explained hereinafter).

Binarization refers to the pixel-wise gray scale transformation according to $$b(x, y) = \begin{cases} 1 & \text{if } g(x, y) \geq thr \\ 0 & \text{otherwise} \end{cases},$$

wherein

| | |
|---|---|
| x | horizontal coordinate of a pixel |
| y | vertical coordinate of a pixel |
| g (x, y) | gray scale value of the pixel at the location (x, y) |
| thr | non-negative threshold value |

The pupil is assumed to be that binary object which exceeds a predetermined minimum and is closest to the image center. Due to its dependence on ambient brightness, a binarization method with a constant threshold value is not suitable. Therefore, binary objects are determined for a series of threshold values according to the above method. The "optimum" threshold value thr* is assumed to be that value which, upon being incremented, results in the smallest change in the selected binary object (i.e. position and size). On the basis of the binary object allocated to this threshold value, the following factors are determined for a rough assessment of the position of the pupil:

$$x_0 = \frac{\sum g(x,y) \cdot x}{\sum g(x,y)} \text{ (Summation over all pixels of the image)}$$

$$y_0 = \frac{\sum g(x,y) \cdot y}{\sum g(x,y)}$$

$$R = \sqrt{\frac{1}{\pi} \sum g(x,y)} \text{ with}$$

$$g(x,y) = \begin{cases} 1(x,y) & \in \text{binary object} \\ 0 & \text{otherwise} \end{cases}$$

| | |
|---|---|
| $(x_0, y_0)$ | centroid of the binary object (center coordinates) |
| R | (area of the binary object/$\pi$)$^{1/2}$ (estimated radius). |

Figure 4:
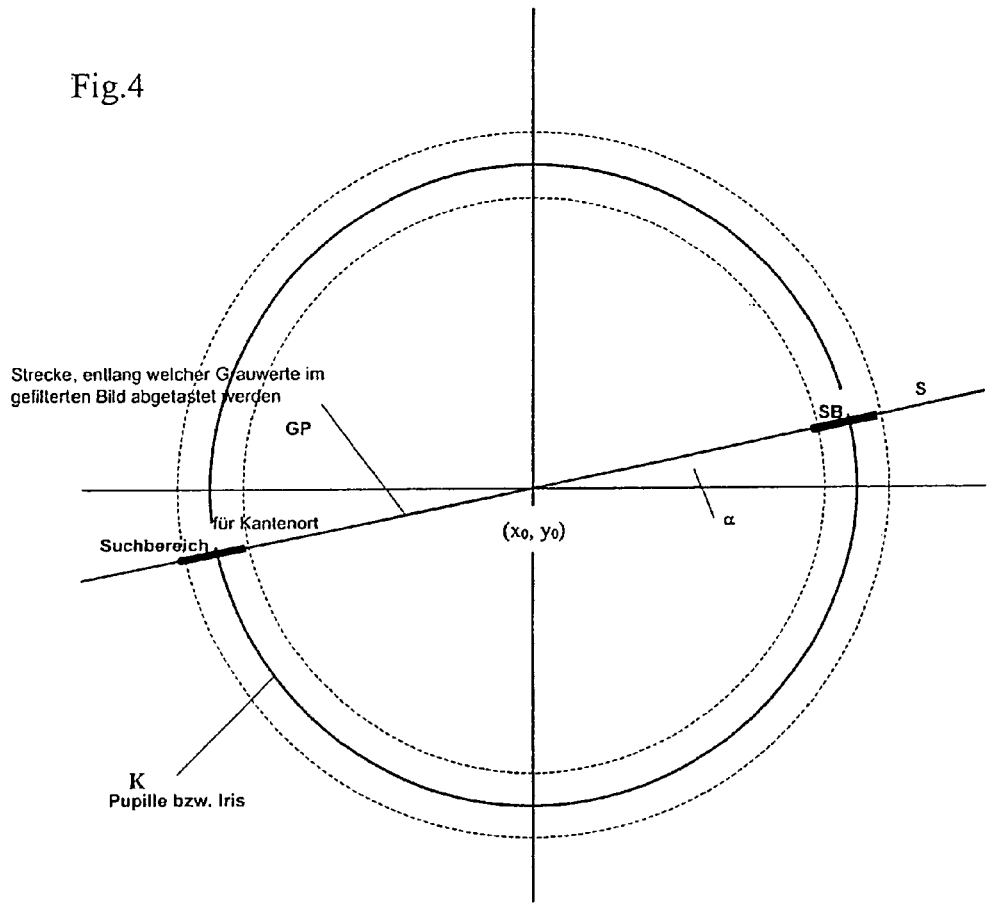
FIG. 4 represents the edge analysis.

Fine Detection of Pupil and Iris—FIG. 4

The edge locations for the pupil and iris (edge="periphery" of the circle/ellipse) are determined from gray scale profiles (=scans of the gray scale values of the median-filtered image along paths) via the center of the roughly determined pupil (see Figure). For the iris, it is assumed, first of all, that the edge is located in a specific, larger circular ring, arranged concentrically to the roughly detected pupil. The following algorithm applies analogously to the fine detection of both the pupil edge and the iris edge.

Scanning was effected by means of search beams (search directions) S starting from xo,yo, with the search beam direction being successively varied by an angle α. The rough search range SB on the search beam S is obtained from the already determined rough model of iris and pupil. The determination of the pupil edge K is effected over the entire circle, while the iris edge determination only takes place in an angular region around the X axis (2 sectors of a circle) due to possible lid covering.

In these profiles, turning points are determined by suitable smoothing and numerical differentiation. A number of methods are known for this purpose (e.g. Savitzky A. and Golay, M. J. E. Analytical Chemistry, Vol. 36, pp. 1627-39, 1964), which may be efficiently implemented as one-dimensional, linear filters. In general, a multiplicity of turning points will be found along the gray scale profile. Among these, that position (x,y) which meets the following conditions is determined as an edge location:

(a) (x,y) is located in a circular ring around $(x_0,y_0)$ (rough position of the pupil) having an internal radius and an external radius, which may be individually determined for the pupil detection and the iris detection, respectively, as a function of r0 (rough radius of the pupil).

(b) The difference, in absolute terms, between the extreme values located around (x,y) in the gray scale profile reaches its maximum at all positions that meet (a).

Thus, a maximum of two edge locations each are available per gray scale profile (i.e. per scanning angle α) for iris modelling and for pupil modelling, respectively. In order to eliminate systematic interferences, for example, caused by the iris or the pupil being covered in the case of a narrow eyelid opening, the range of scanning angles used may be restricted, i.e. $\alpha_{min, iris} < \alpha < \alpha_{max, iris}$ for iris edge determination and, analogously, $\alpha_{min, pupil} < \alpha < \alpha_{max, pupil}$ for pupil edge determination.

Figure 5:
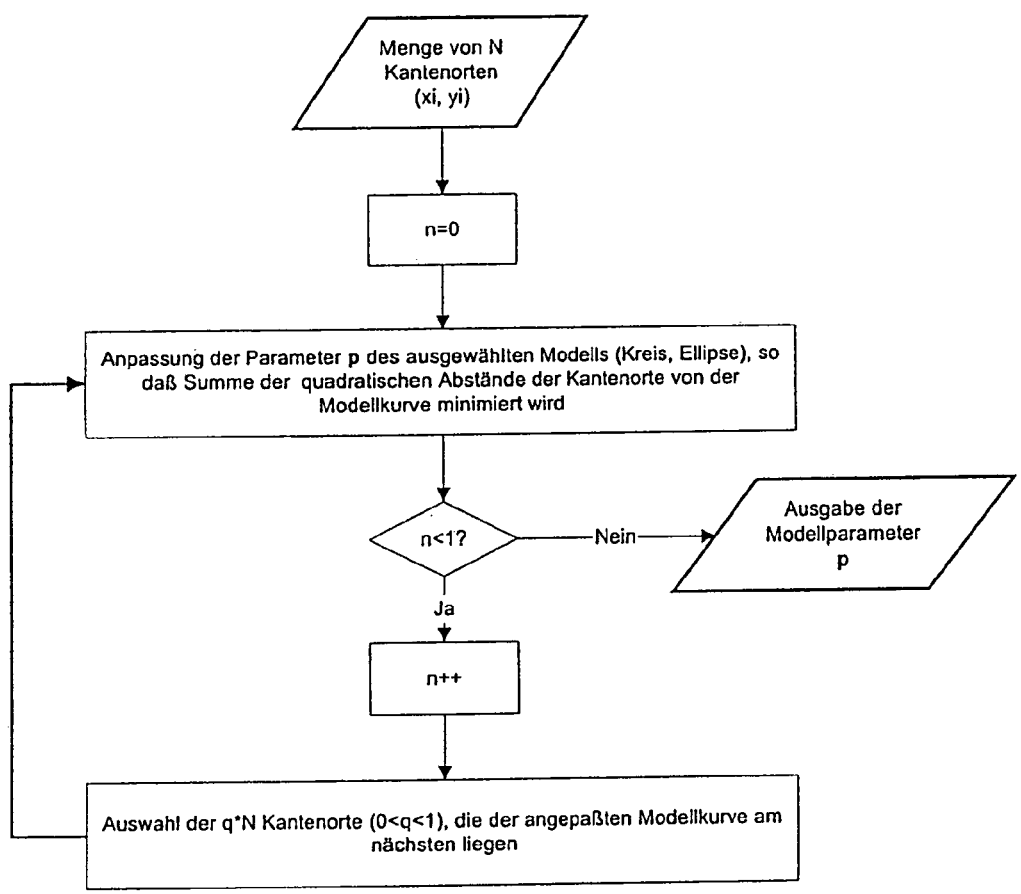
FIG. 5 is a flowchart of the edge analysis.

Adaptation of the Pupil/Iris Model—FIG. 5

The number of edge locations (xi, yi) determined in the preceding step allows the parameters of the pupil model and of the iris model (i.e. either circle or ellipse) to be determined by means of regression. This is done by minimizing the sum of square errors $$\sum_i (x_i - x(x_i, y_i, p))^2 + (y_i - y(x_i, y_i, p))^2 \to \min \quad (1)$$

over the number of possible parameter vectors p (circle: center coordinates and radius; ellipse: center coordinates, lengths of the main axes, angle(s) between the great main axis and the x axis). For adjustment of the circle, a solution of (1) is possible in a direct and numerically efficient manner by the method of singular value distribution. For the solution of the restricted root-mean-square value problem for adaptation of the ellipse, there also exist a number of standard approaches (e.g. in Bookstein, F. L. Fitting conic sections to scattered data. Computer Graphics and Image Processing, Vol. 9, pp. 56-71, 1979, and Fitzgibbon, A. W. and Fisher, R. B. A buyer's guide to conic fitting. Proceedings of British Machine Vision Conference, Birmingham, 1995).

In order to reduce the influence of wild values (i.e. incorrectly determined edge locations), use is made of a two-step regression method according to FIG. 5.

Moreover, alternative methods for selection of the edge locations which are to be used for parameter adaptation can be used, such as the Hough transformation for circular models.

Figure 6:
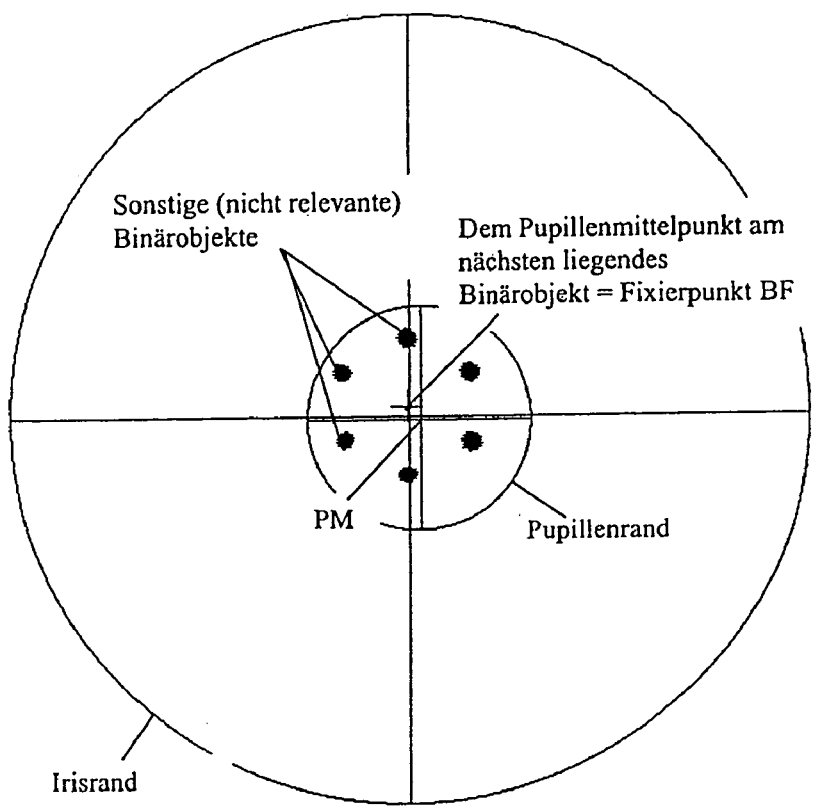
FIG. 6 shows the detection and determination of the fixation point position.

Detection of the Fixation Point—FIG. 6

For detection of the fixation point, a binarization (see above) of the unfiltered image of the CCD camera is effected with a threshold value $\Theta_{FP} = s \cdot thr^*$ (s>1.0), said threshold value depending on thr* (threshold value used for the rough detection of the pupil). As the fixation point, there is determined the center of that integral binary object BF (gray scale values $> \Theta_{FP}$) which is located closest to the determined pupil center PM and has a predetermined minimum surface area.

Other, non-relevant binary objects (e.g. reflection images of the LED illumination) are identified through their greater distance from the pupil center and are not taken into consideration.

Figure 7:
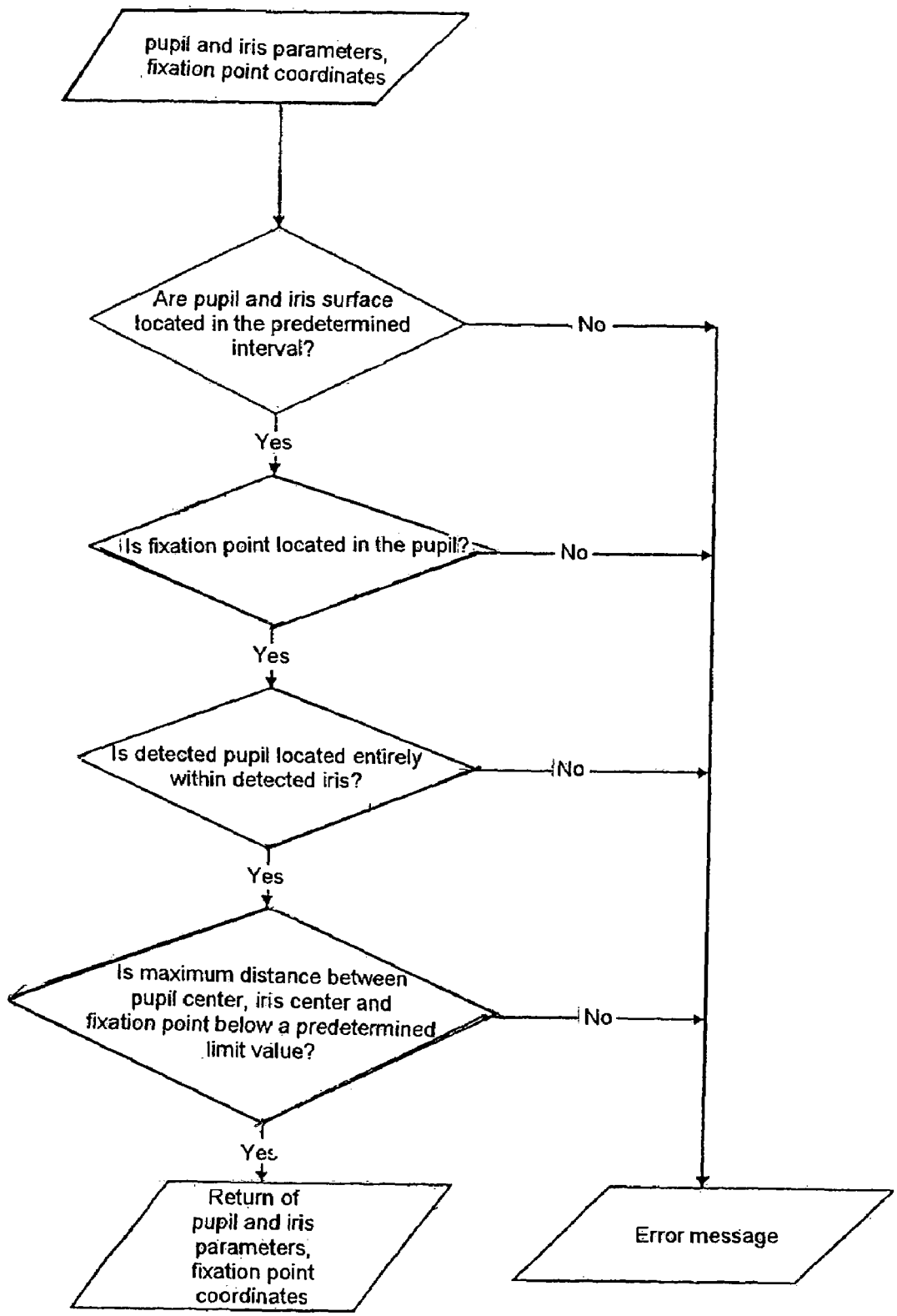
FIG. 7 is a flowchart of the plausibility check.
Figure 1:
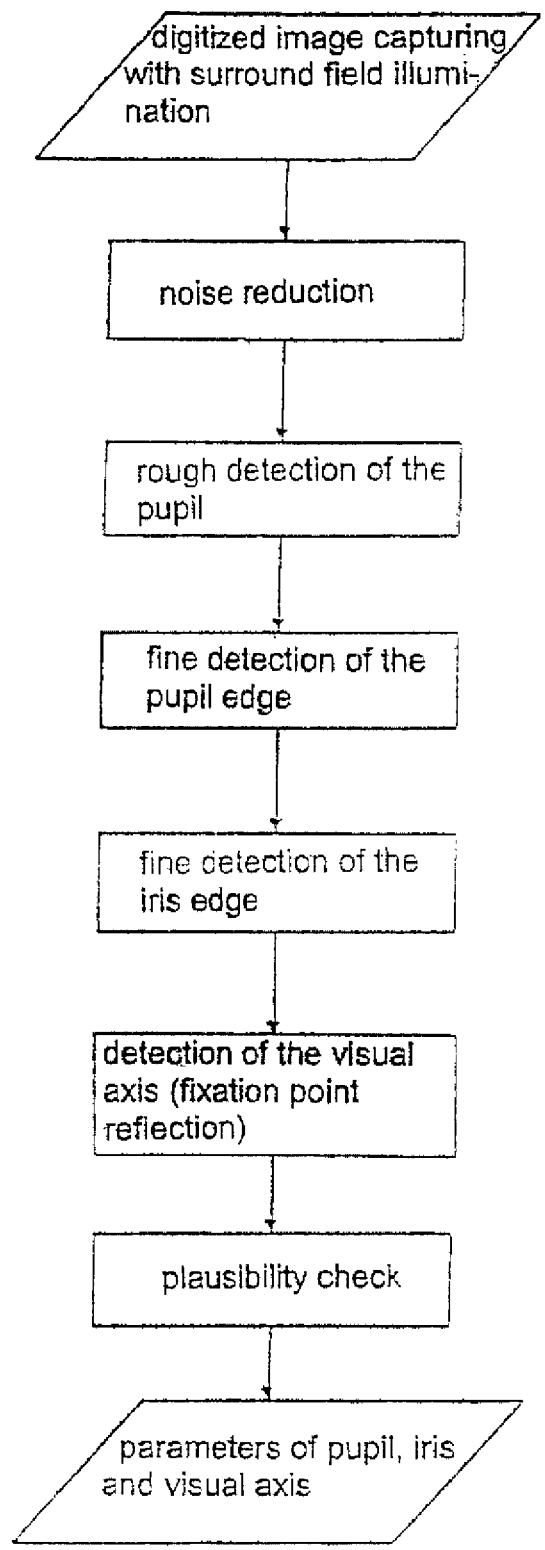
Figure 2:
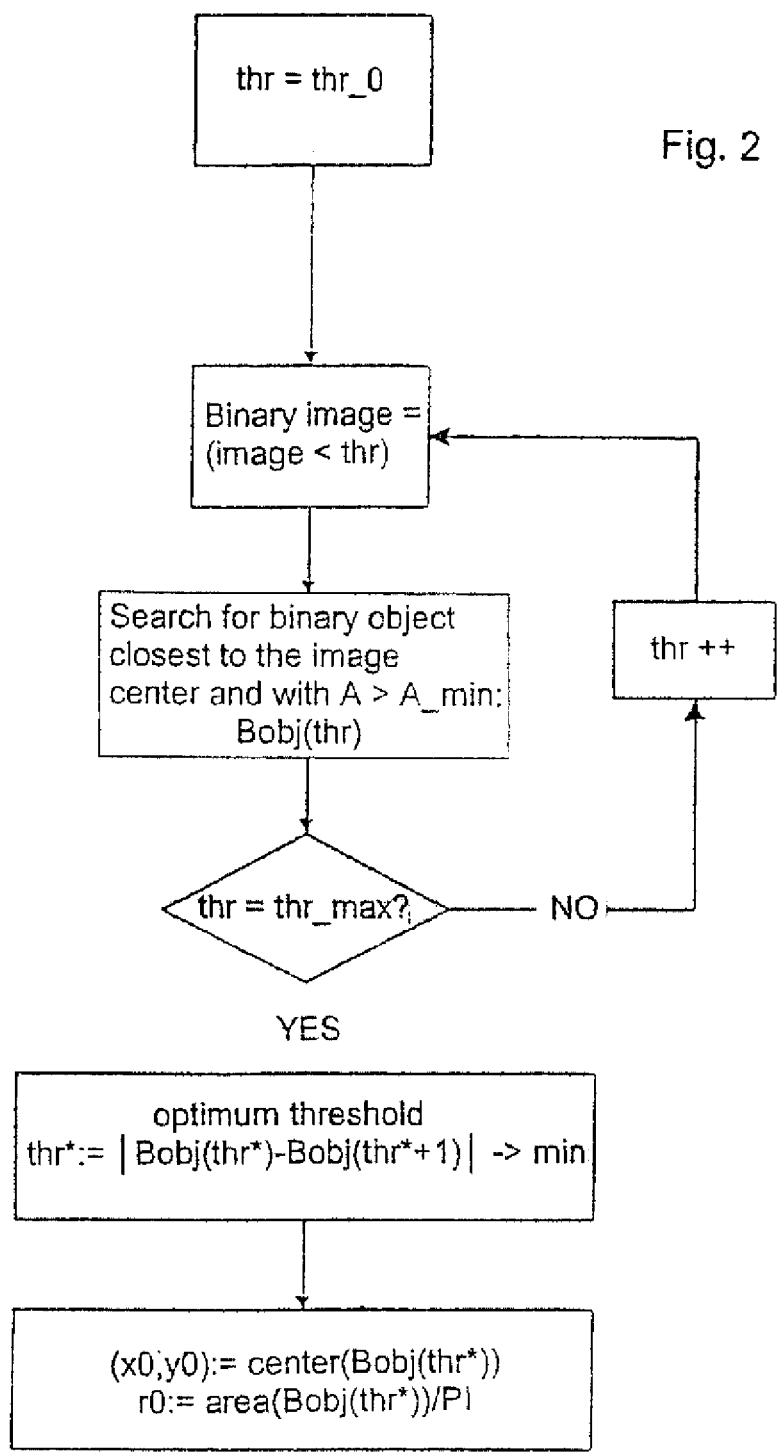
Figure 3:
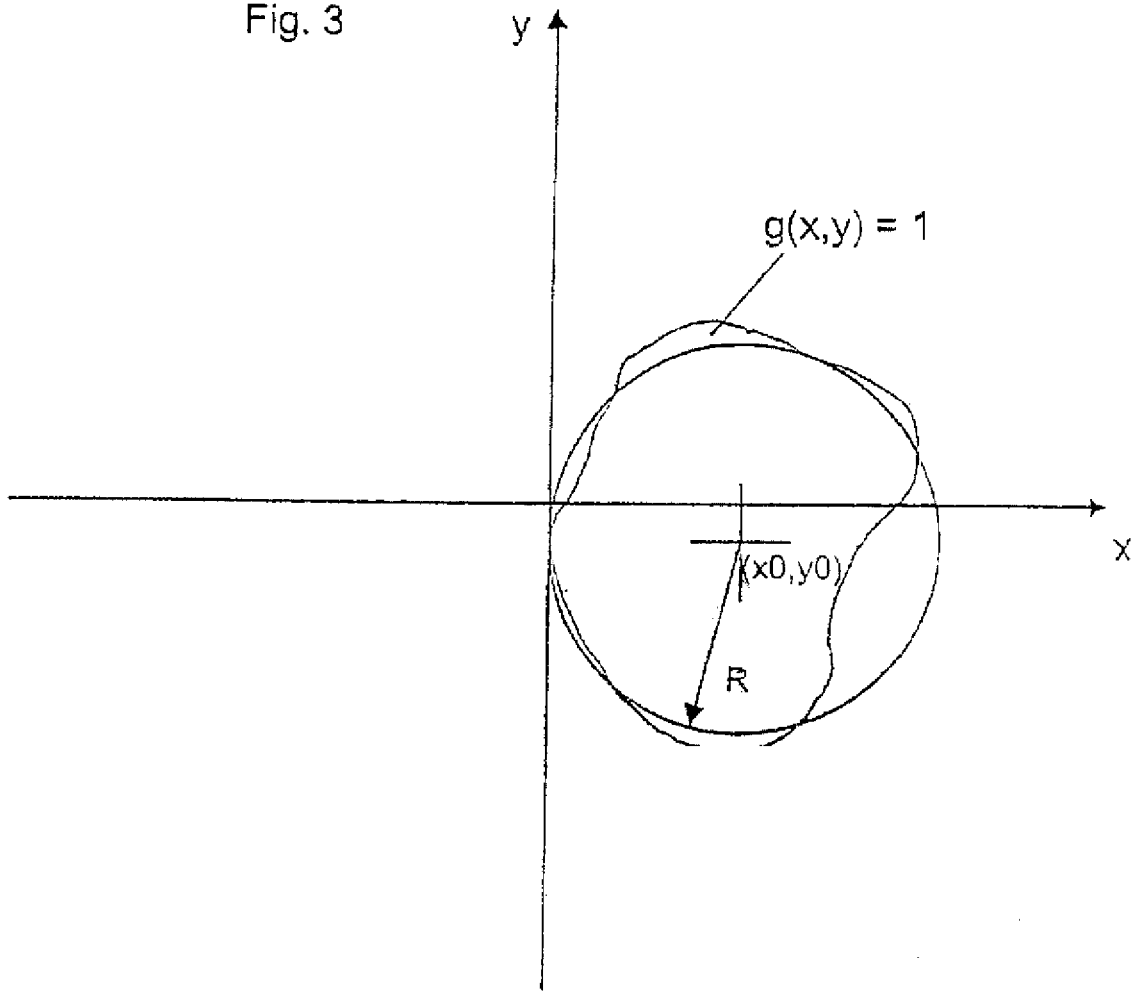
Figure 5:
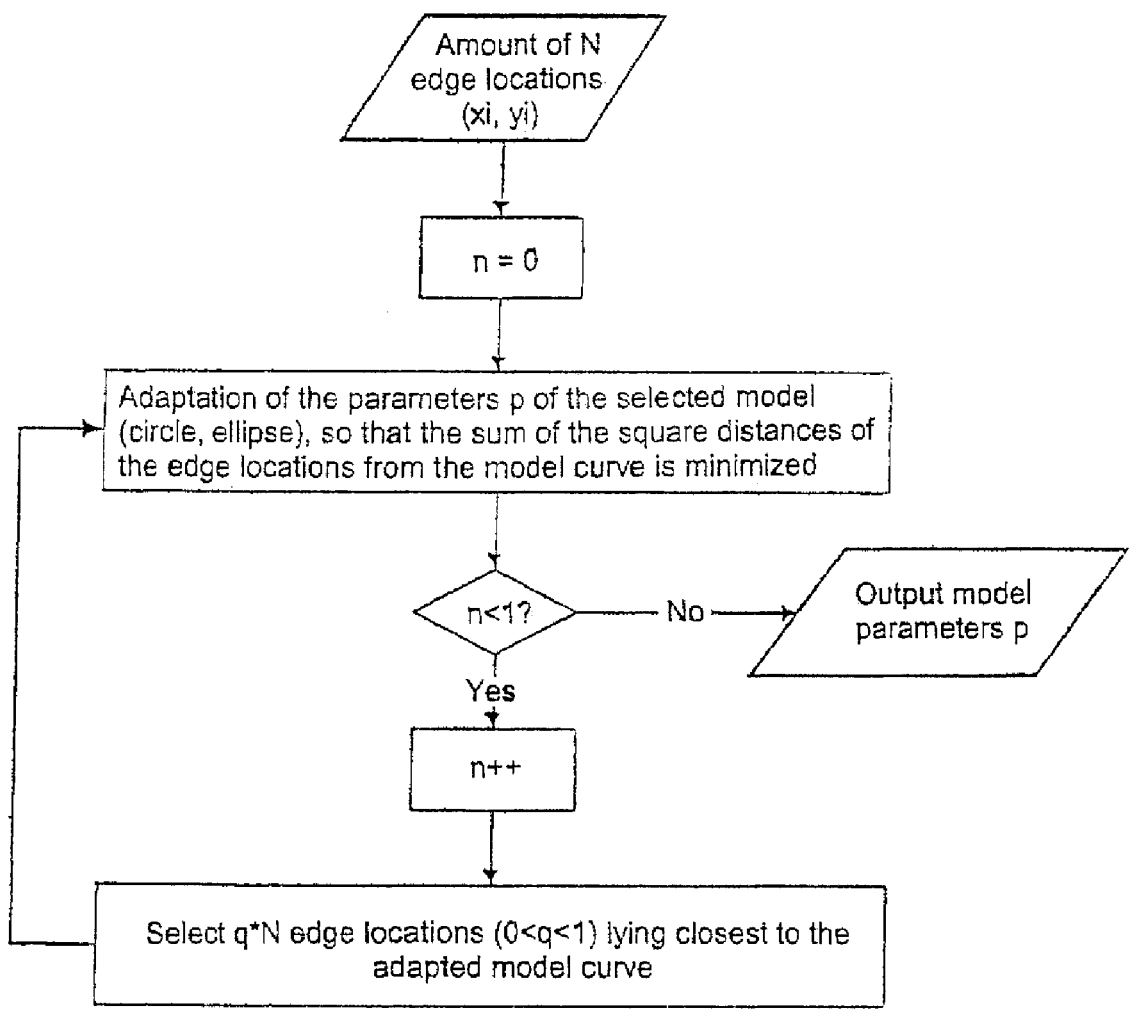
Figure 6:
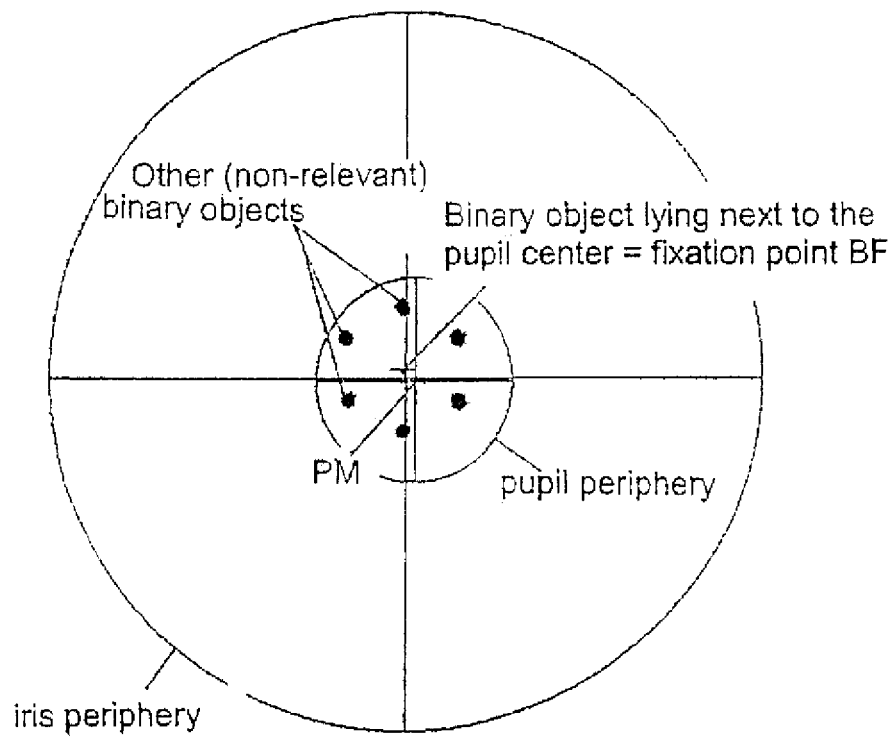
Figure 7:
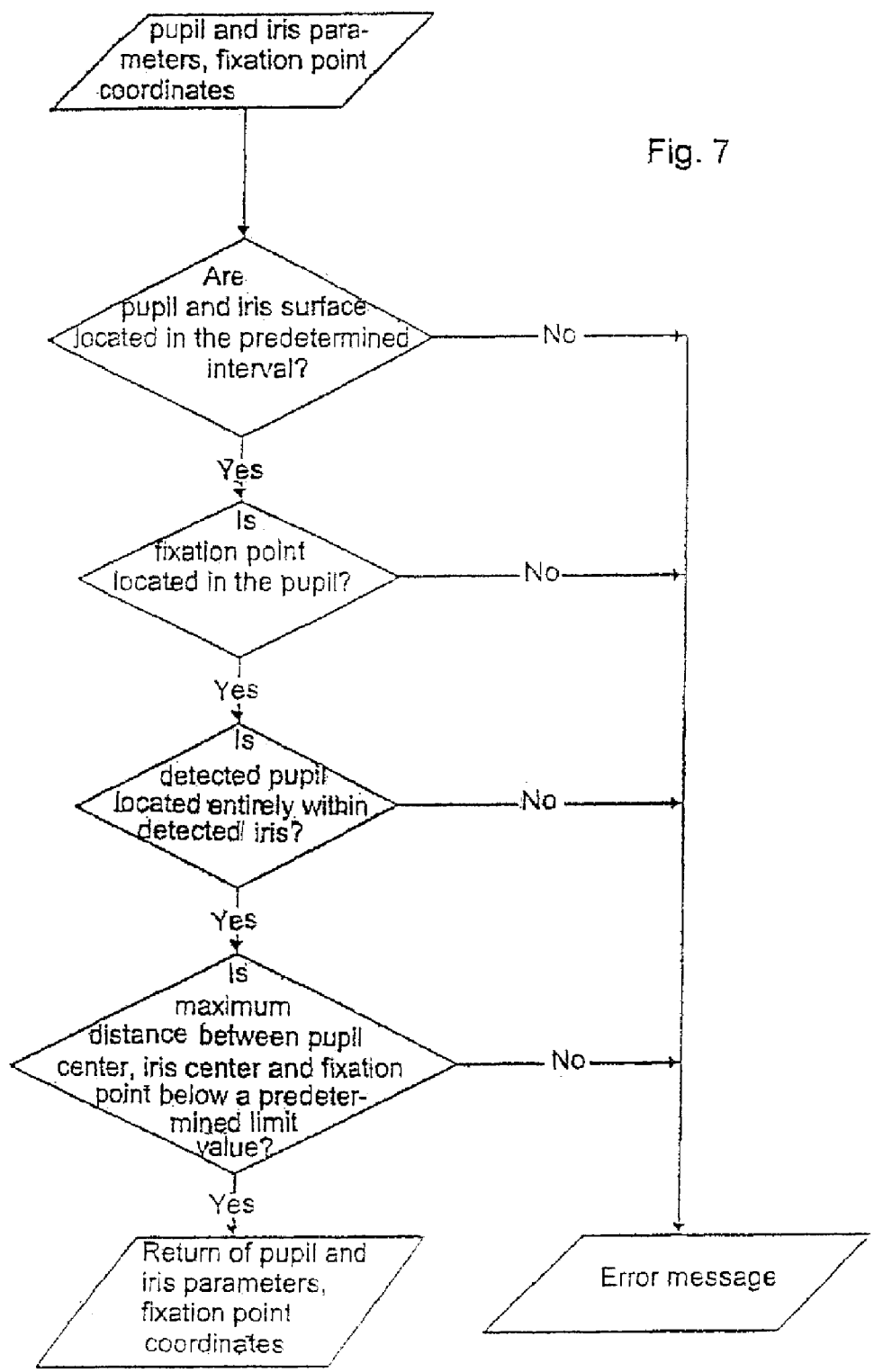

Plausibility Check—FIG. 7

Before the determined coordinates are returned to the calling program, a plausibility check according to FIG. 7 is effected in order to prevent that possibly incorrectly detected elements are found. Interrogations comprise previously known properties of the examined object, with which the determined results must be coincident.

Fig. 11 White-to-white gauge according to Holladay-Godwin: AE-1576 Holladay-Godwin Cornea Gauge
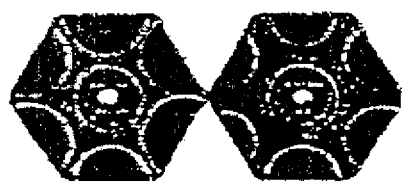

The invention claimed is:

1. A method for measuring a pupil diameter and/or an iris diameter, comprising of:

capturing an image of at least part of the eye with an image capture unit and an illumination system;

digitizing the captured image;
determining rough values of a pupil center and a radius of the pupil via an intensity threshold analysis; and
performing a fine detection of edges of the pupil and/or an iris on the basis of the rough determination
wherein the fine detection comprises
scanning the digitized captured image along linear paths generally crossing the roughly detected pupil center wherein edges are detected along the linear paths and wherein the linear paths are within a limited angular region around a horizontal axis of the pupil; and
modeling the iris and the pupil by using a generally circular or a generally elliptic model of the edges of the iris and the pupil.

2. The method as claimed in claim 1, in which the structure whose edges are finely detected is selected from a group consisting of the pupil and the iris.

3. The method as claimed in claim 1, further comprising the step of determining an intersection point of a visual axis of the eye with a cornea by the use of a fixation light.

4. The method as claimed in claim 1, further comprising the step of determining an intersection point of a visual axis with the cornea with relation to the pupil or the iris on the basis of a position of a fixation reflection.

5. The method as claimed in claim 1, further comprising the step of determining an angle between a visual axis of the eye and an optical axis of the eye based on a position of a fixation reflection relative to a center of the pupil or a center of the iris.

6. The method as claimed in claim 5, further comprising the step of preadjusting an instrument for interferometric measurement of the segments of the eye along the optical axis of the eye using the angle determined.

7. A device for measuring a pupil diameter and/or an iris diameter, comprising:
an image capture unit to capture an image of at least a portion of the eye;
an illumination system to illuminate the eye to facilitate the image capture;
a digitizer to digitize the captured image;
a microprocessor; and
software adapted to direct the microprocessor to determine rough values of a pupil center and a radius of the pupil; and subsequently, a fine detection analysis to determine the position of the edges of the structure based on the rough location
wherein the fine detection comprises:
scanning the digitized captured image alone linear paths generally crossing the roughly detected pupil center wherein edges are detected along the linear paths and wherein the linear paths are within a limited angular region around a horizontal axis of the pupil; and
modeling the iris and the pupil by using a generally circular or a generally elliptic model of the edges of the iris and the pupil.

8. The device as claimed in claim 7, in which the structure of whose edges are finely detected is selected from a group consisting of the pupil and the iris.

9. The device as claimed in claim 7, further comprising software to direct the microprocessor to determine an intersection point of a visual axis with the cornea by the use of a fixation light.

10. The device as claimed in claim 7, further comprising software to direct the microprocessor to determine an intersection point of a visual axis with the cornea with relation to the pupil or the iris on the basis of a position of a fixation reflection.

11. The device as claimed in claim 7, further comprising software to direct the microprocessor to determine an angle between a visual axis of the eye and an optical axis of the eye based on a position of a fixation reflection relative to a center of the pupil or a center of the iris.

12. The device as claimed in claim 11, further comprising software to direct the microprocessor to preadjust an instrument for interferometric measurement of the segments of the eye along the optical axis of the eye using the angle determined.

13. A device for measuring a pupil diameter and/or an iris diameter, comprising:
means for capturing an image of at least part of the eye;
means for illuminating the eye;
means for digitizing the captured image;
means for performing rough values of a pupil center and a radius of the pupil via an intensity threshold analysis; and
means for performing a fine detection of edges of the structure on the basis of the rough determination
wherein the fine detection comprises:
scanning the digitized captured image along linear paths generally crossing the roughly detected pupil center wherein edges are detected along the linear paths and wherein the linear paths are within a limited angular region around a horizontal axis of the pupil; and
modeling the iris and the pupil by using generally circular or a generally elliptic model of the edges of the iris and the pupil.

14. The device as claimed in claim 13, in which the structure whose edges are finely detected is selected from a group consisting of the pupil and the iris.

15. The device as claimed in claim 13, further comprising means for determining an intersection point of a visual axis with the cornea by the use of a fixation light.

16. The device as claimed in claim 13, further comprising means for determining an intersection point of a visual axis with the cornea with relation to the pupil or the iris on the basis of a position of a fixation reflection.

17. The device as claimed in claim 13, further comprising means for determining an angle between a visual axis of the eye and an optical axis of the eye based on a position of a fixation reflection relative to a center of the pupil or a center of the iris.

18. The device as claimed in claim 17, further comprising means for preadjusting an instrument for interferometric measurement of the segments of the eye along the optical axis of the eye using the angle determined.

* * * * *

UNITED STATES PATENT AND TRADEMARK OFFICE
CERTIFICATE OF CORRECTION

| | | |
|---|---|---|
| PATENT NO. | : 7,284,858 B2 | |
| APPLICATION NO. | : 10/468241 | |
| DATED | : October 23, 2007 | |
| INVENTOR(S) | : Bergner et al. | |

It is certified that error appears in the above-identified patent and that said Letters Patent is hereby corrected as shown below:

Title page, illustrative figs. 4 and 8 should be deleted and substitute therefore the attached title page consisting of the attached illustrative figs. 4 and 8.

The drawing sheets 1-9 consisting of Fig(s) 1-9 should be deleted and substitute therefore the attached drawing sheets 1-9 consisting of Fig(s) 1-9.

Signed and Sealed this

Twenty-ninth Day of December, 2009

David J. Kappos
*Director of the United States Patent and Trademark Office*

United States Patent
Bergner et al.

(10) Patent No.: US 7,284,858 B2
(45) Date of Patent: Oct. 23, 2007

(54) METHOD FOR DETERMINING DISTANCES IN THE ANTERIOR OCULAR SEGMENT

(75) Inventors: Roland Bergner, Jena (DE); Roland Barth, Jena (DE); Axel Duering, Jena (DE); Frank Behrend, Jena (DE); Klaus-Ditmar Voigt, Jena (DE)

(73) Assignee: Carl Zeiss Meditec AG, Jena (DE)

(*) Notice: Subject to any disclaimer, the term of this patent is extended or adjusted under 35 U.S.C. 154(b) by 630 days.

(21) Appl. No.: 10/468,241

(22) PCT Filed: Feb. 16, 2002

(86) PCT No.: PCT/EP02/01675

§ 371 (c)(1),
(2), (4) Date: Aug. 18, 2003

(87) PCT Pub. No.: WO02/065899

PCT Pub. Date: Aug. 29, 2002

(65) Prior Publication Data
US 2004/0070728 A1    Apr. 15, 2004

(30) Foreign Application Priority Data
Feb. 21, 2001 (DE) .................. 101 08 797

(51) Int. Cl.
A61B 3/10 (2006.01)

(52) U.S. Cl. .................. 351/205; 351/206; 351/208

(58) Field of Classification Search .......... 351/205, 351/206, 208–212, 221, 246; 396/51; 382/103, 382/117, 128, 276
See application file for complete search history.

(56) References Cited

U.S. PATENT DOCUMENTS 4,319,564 A    3/1982    Karickhoff (Continued)

FOREIGN PATENT DOCUMENTS

DE    196 41 632 A1    5/1997

(Continued)

OTHER PUBLICATIONS

International Search Report.

Primary Examiner—Huy Mai
(74) Attorney, Agent, or Firm—Patterson, Thuente, Skaar & Christensen, P.A.

(57) ABSTRACT

The invention relates to a method for determining distances in the anterior ocular segment, preferably of the pupils and/or the diameter of the iris, wherein the image of at least part of the eye is recorded and digitized using an imaging device and an array for illuminating the eye. On the basis of said digital image, a center of gravity analysis and the determination of the central point are carried out, especially for the position of the pupils, by conducting an intensity and threshold analysis as rough determination. Based on said rough determination, a fine detection of the position of the edges of the pupil and/or the edges of the iris is carried out. Additionally, the angle between the visual axis and the optical axis of the eye can be determined from the position of a fixed reflection to the center of the pupil and/or the center of the iris.

18 Claims, 9 Drawing Sheets

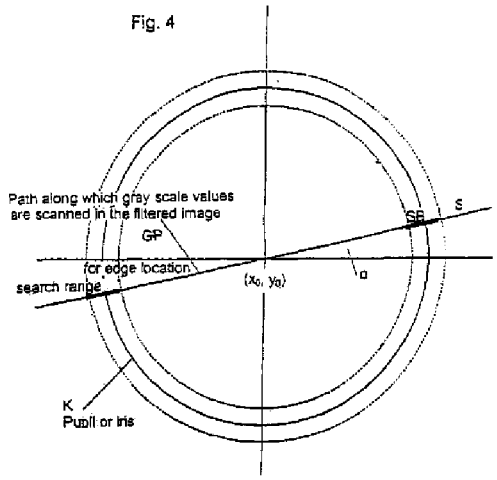

Fig. 4

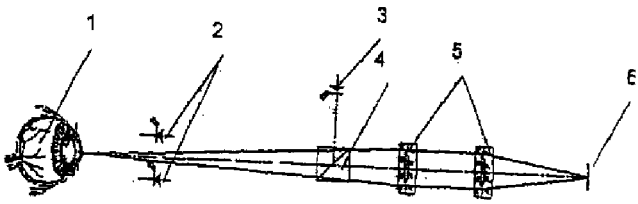

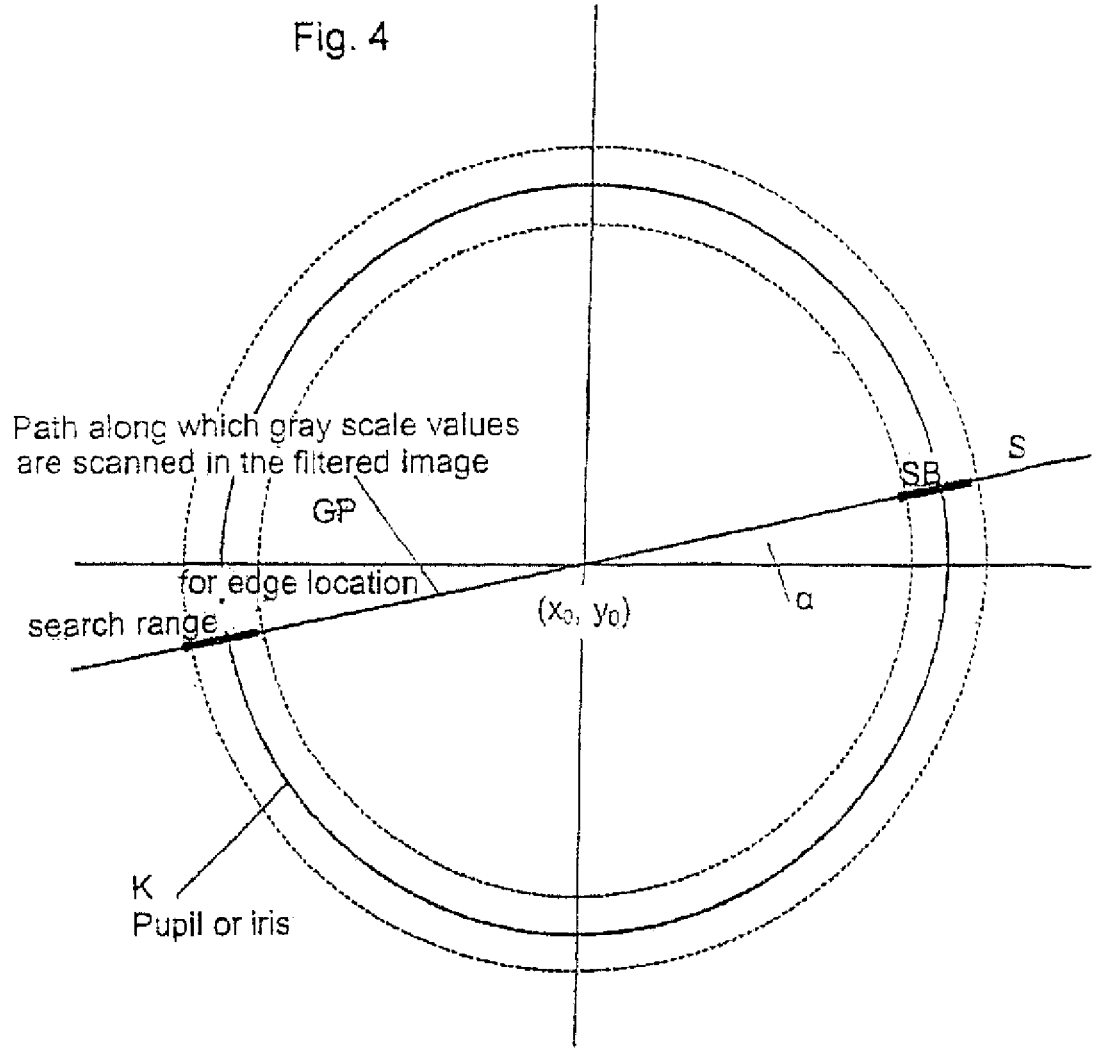

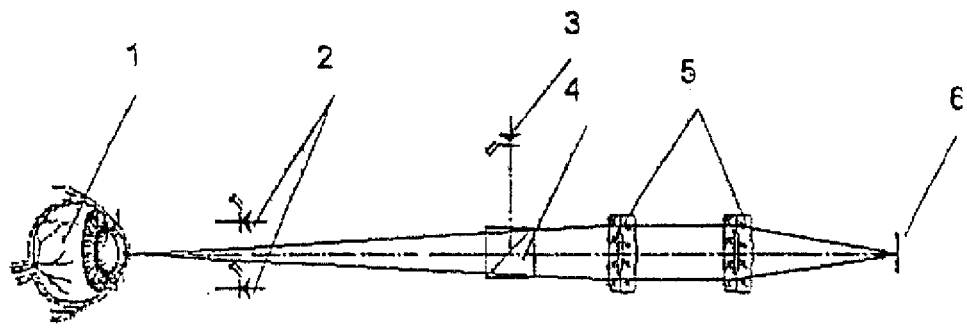
Fig. 8 schematic representation of the arrangement according to the invention
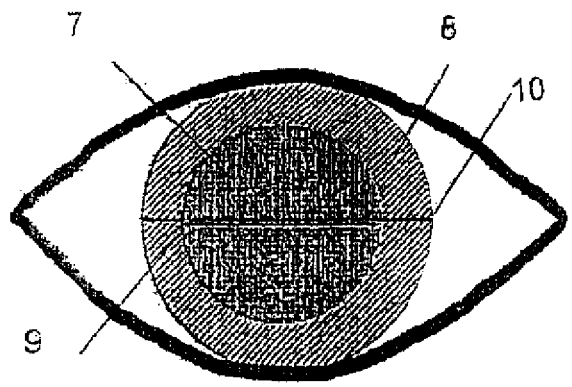
Fig. 9 grabbed image of an eye to be measured
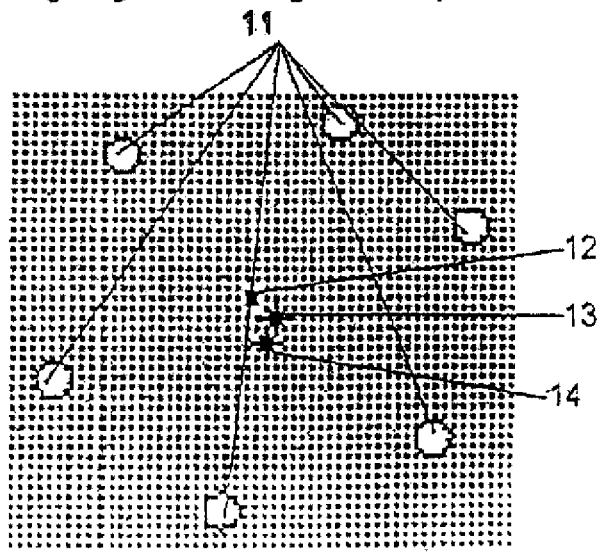
Fig. 10 enlargement of central part of Fig. 9